United States Patent
Behiels

(10) Patent No.: US 9,155,507 B2
(45) Date of Patent: Oct. 13, 2015

(54) METHOD TO DETECT AND INDICATE INACCURACIES IN LONG LENGTH IMAGING

(75) Inventor: Gert Behiels, Edegem (BE)

(73) Assignee: Agfa HealthCare NV, Mortsel (BE)

( * ) Notice: Subject to any disclaimer, the term of this patent is extended or adjusted under 35 U.S.C. 154(b) by 118 days.

(21) Appl. No.: 14/125,338

(22) PCT Filed: Jun. 14, 2012

(86) PCT No.: PCT/EP2012/061324
§ 371 (c)(1),
(2), (4) Date: Dec. 11, 2013

(87) PCT Pub. No.: WO2012/172006
PCT Pub. Date: Dec. 20, 2012

(65) Prior Publication Data
US 2014/0093044 A1    Apr. 3, 2014

Related U.S. Application Data

(60) Provisional application No. 61/497,766, filed on Jun. 16, 2011.

(30) Foreign Application Priority Data

Jun. 16, 2011   (EP) .................................... 11170103

(51) Int. Cl.
A61B 6/00    (2006.01)
A61B 6/02    (2006.01)
G06T 3/40    (2006.01)

(52) U.S. Cl.
CPC ................. *A61B 6/02* (2013.01); *A61B 6/5229* (2013.01); *A61B 6/5241* (2013.01); *A61B 6/5264* (2013.01); *G06T 3/4038* (2013.01)

(58) Field of Classification Search
CPC .. A61B 6/5229; A61B 6/5235; A61B 6/5241; A61B 6/5258; A61B 6/5264
See application file for complete search history.

(56) References Cited

U.S. PATENT DOCUMENTS

| | | | | | |
|---|---|---|---|---|---|
| 5,123,056 | A | * | 6/1992 | Wilson | 382/132 |
| 5,986,279 | A | * | 11/1999 | Dewaele | 250/582 |
| 2005/0129298 | A1 | * | 6/2005 | Warp et al. | 382/132 |
| 2008/0152088 | A1 | * | 6/2008 | Wang et al. | 378/98.12 |
| 2009/0123892 | A1 | * | 5/2009 | Sogo et al. | 433/213 |
| 2011/0038454 | A1 | * | 2/2011 | Minnigh et al. | 378/62 |
| 2011/0064193 | A1 | * | 3/2011 | Minnigh et al. | 378/62 |
| 2013/0077749 | A1 | * | 3/2013 | Akahori et al. | 378/62 |
| 2014/0093044 | A1 | * | 4/2014 | Behiels | 378/62 |

* cited by examiner

*Primary Examiner* — Thomas R Artman
(74) *Attorney, Agent, or Firm* — Keating & Bennett, LLP

(57) ABSTRACT

Method of generating radiation images of an elongate body by applying different computer-implemented stitching methods to the same set of partial radiation images. A warning is generated in case of substantial deviation between the applied stitching methods.

5 Claims, 5 Drawing Sheets

METHOD TO DETECT AND INDICATE INACCURACIES IN LONG LENGTH IMAGING

RELATED APPLICATIONS

This application is a §371 National Phase Application of International Application No. PCT/EP2012/061324, filed on Jun. 14, 2012, now International Publication No. WO 2012/172006 A2, published on Dec. 20, 2012, which International Application claims the benefit under 35 U.S.C. §119(e) of U.S. Provisional Application No. 61/497,766, filed on Jun. 16, 2011, and also claims priority to European Application No. EP 11170103.3, filed on Jun. 16, 2011, all three of which are incorporated herein by reference in their entirety.

FIELD OF THE INVENTION

The present invention relates to a method for generating an x-ray image of an elongate body in direct radiography by generating a plurality of partial x-ray images of said elongated body and by stitching these partial images. More specifically the invention relates to the case in which patient movement or system mis-calibration occurs.

BACKGROUND OF THE INVENTION

In X-ray radiography an x-ray image of an elongate body such as the entire spine or the legs of a patient, may have to be obtained. Long length images are mostly taken to perform length and angle measurements on a radiation image of a subject.

In Computed Radiography (CR), such a long length image is generated by subjecting a number of Imaging Plates (IP), such as photo-stimulable phosphor plates, which are organized in a partially overlapping disposition, to an x-ray image of the elongate body. Each of the imaging plates carries an image of a part of the elongate body. After exposure, the individual imaging plates are read out so as to obtain partial images of the elongate body and finally a long length image is created by stitching these partial images. Accurate alignment and measurement can be obtained by superimposing an object of known geometry of radiation attenuating material such as a grid covering the region to be imaged and correcting and aligning the partial images to reconstruct the geometry of said grid. Such methods are described in European patent applications EP0919856 and EP0866342.

In recent years, Digital Radiography (DR) has become a valuable alternative for CR. The flat panel detectors (FPD) used in DR are more costly than the IP's for CR, so an alternative to the one-shot long length imaging technique of CR is needed. This is achieved by taking plural partial images of an elongate body by moving the position of the FPD while tilting the X-ray tube or moving the X-ray tube parallel to the FPD. During this movement, the patient may move, hereby introducing artifacts which need to be compensated in the full image re-composition from the partial images. The applied compensations for the correction of the patient movement may lead to inaccurate measurements. Inaccurate FPD positioning also decreases the accuracy of measurements done in the composite image.

An article by Xiaohui Wang, "Fully automatic and reference-marker-free image stitching method for full-spine and full-leg imaging with computed radiography", Proceedings of SPIE, vol. 5368, 1 Jan. 2004, pages 361-369 discloses image stitching of partial images.

In the article by Simon T. Y. Suen et al, "Photographic stitching with optimized object and color matching based on image derivatives", Optics Express, Vol. 15, No. 12, 1 Jun. 2007, different stitching methods are compared. The article discloses a theoretical comparison.

It is an object of the present invention to overcome the drawbacks of the prior art.

SUMMARY OF THE INVENTION

The above-mentioned aspects are realized by a method having the specific features set out in claim 1.

According to the invention a method is disclosed in which different computer-implemented stitching methods are applied to a set of partial radiation images generated of the elongate body. The deviation between these stitching methods is determined (by calculating a measure indicative of this deviation) and a computer-controlled warning (auditive, visual, . . . ) is generated if this deviation exceeds a preset acceptance value (also called threshold).

The method of the present invention is suitable for detecting patient movement and generating a warning in case patient movement has occurred in between the recording of partial radiation images of a body. The warning set out in claim 1 may be an indication of patient movement. From another point of view this method can be seen as a method for detecting patient movement during radiation image recording and generating a warning in case of patient movement.

In the context of this invention, an elongate body is a body the projection x-ray image of which cannot be taken by means of a single x-ray exposure of an x-ray detector. The radiation image of such an elongate body is composed by applying a computer-implemented stitching method to a set of partial radiation images each comprising part of the radiation image of the elongate body. An elongate body is for example a full leg or a full spine.

Different stitching methods may be envisaged.

A first stitching methods is a computer-implemented stitching method based on theoretical stitching parameters originating from the set-up of the x-ray source and the detector (positioning, distance, angle) when the multiple shot irradiation is performed.

Another computer-implemented stitching method is based on the reconstruction of the image of an object of known geometry such as a grid of x-ray attenuating material that is recorded together with the partial images of the elongate body so that each partial image comprises part of the radiation image of the elongate body and part of the radiation image of the object of known geometry. The complete radiation image of the elongate body can then be composed by means of a computer-implemented reconstructing the image of the object of known geometry thereby also reconstructing the composed image of the elongate body by means of the partial images.

Still another stitching method is a method in which the complete image of the elongate body is reconstructed from the partial radiation images on the basis of user interaction (i.e. the positioning or aligning of the partial images by the user). The user positions either manually or by means of an automated system the partial images in order to reconstruct the complete image of the elongate body. The user can thus correct effects caused by patient movement in between multiple partial exposures.

Still other methods may be envisaged.

Specific features for preferred embodiments of the invention are set out in the dependent claims.

Further advantages and embodiments of the present invention will become apparent from the following description and drawings.

DETAILED DESCRIPTION OF THE INVENTION

Long length images of an elongate body are mostly taken to perform length and angle measurements on the subject across an area larger than a single FPD. A set of partial images is then created and stitched by means of a computer-implemented stitching method applied to the digital signal representations of the partial images.

It is important to create a long length image where the alignment of the partial images of the elongate body in the resulting image is accurate.

Measurement inaccuracies are caused by the inaccuracies of the system and/or by patient movement.

Figure 1:
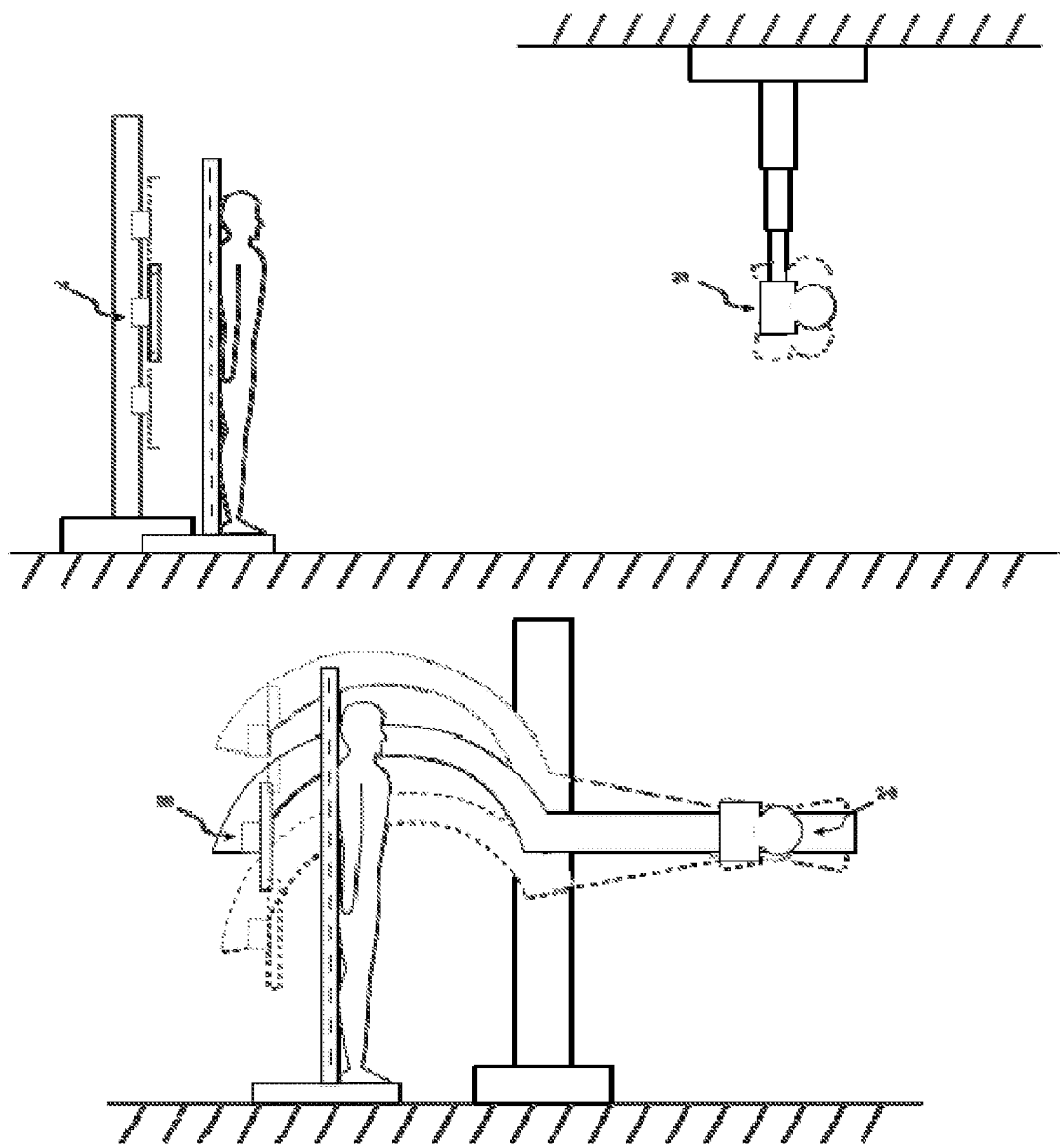
FIG. 1 are illustrations of systems typically used to perform long length imaging.
Figure 2:
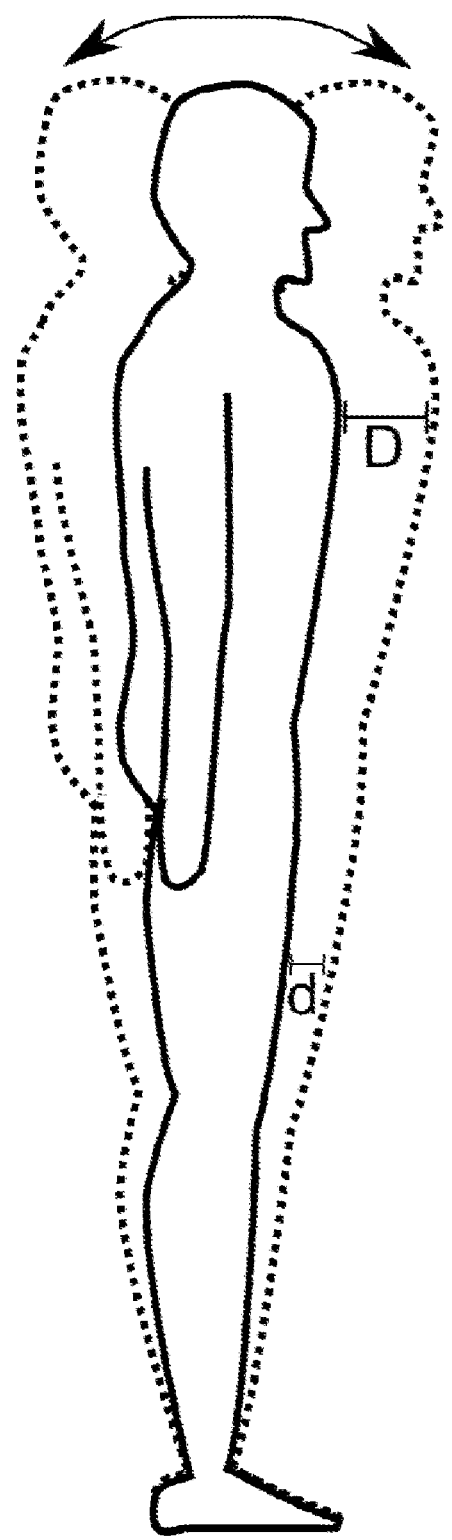
FIG. 2 illustrates a degree of freedom for patient movement.

Some typical configurations for systems capable to perform long length imaging are illustrated in FIG. 1. The inaccuracies of the system are mostly related to inaccurate positioning of the X-ray Imaging Unit (10) or the X-ray generation unit (20). If an object of known geometry is imaged together with the elongate body, inaccuracies of the positions can be estimated by comparison of the parameters to stitch the partial images of the object of known geometry with the parameters derived from the geometry and the positions of the system.

Because the acquisition of the partial images takes some time, the patient will not be able to stand perfectly still. Some methods exists to minimize the amount of corrections needed to compensate for the patient movement (see co-pending patent application entitled 'Method of generating a radiation image of an elongate body' filed on Apr. 7, 2011) but none of these are capable to prevent patient movement.

Comparison between stitch parameters derived from the positions of the system or from the object of known geometry and stitch parameters given by the user or automatically extracted from the subject's projection in the image is a valuable indicator of the amount of patient movement.

Detection of System Inaccuracies

One embodiment of the method of the present invention is based on the use of a radiation image of an object of known geometry superposed on the radiation image of the elongate body.

Figure 3:
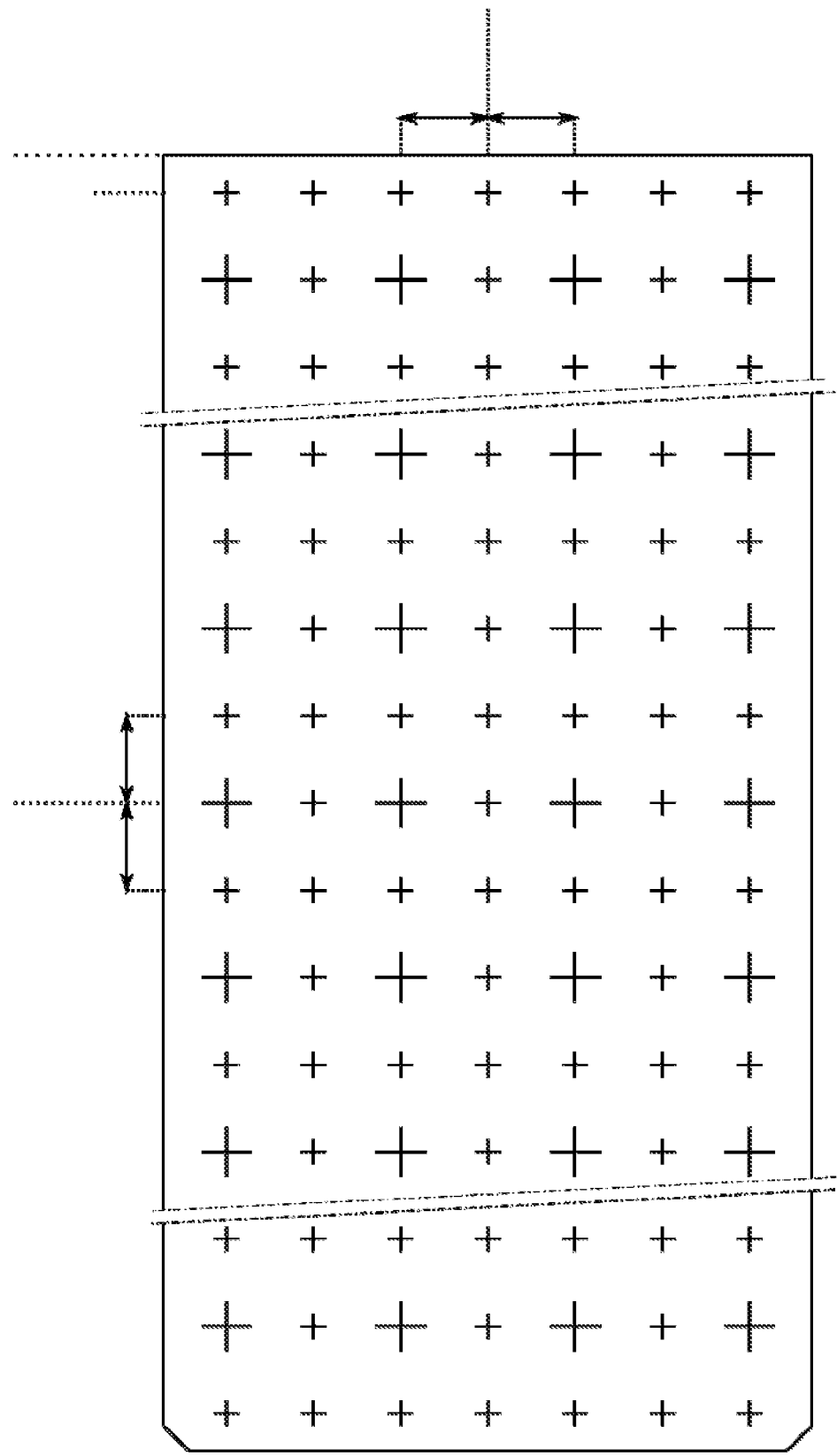
FIG. 3 is a design of a radio translucent plate with X-ray attenuating crosses placed on a regular grid of 5 by 5 cm.

An example of an object of known geometry which can be used in the present invention is a radio translucent plate with crosses placed on a regular grid of 5 by 5 cm as is shown in FIG. 3.

A radiation image of the elongate body is obtained by generating partial radiation images by multiple shot irradiation and read out of a radiation detector whereby each of the partial images comprises part of the radiation image of the elongate body and part of the radiation image of an object of known geometry. The partial images are then stitched to generate the complete image of the elongate body.

The complete image of the elongate body and of the object of known geometry is then used to perform an estimation of the inaccuracies.

Assume that two partial images A and B have been acquired and that the stitched image is then created by placing the top left corner pixel of image B at pixel position $(x_s, y_s)$ in image A and merging the overlapping pixels with a known merging technique. It is clear that for each position $(x_s, y_s)$, a different stitched image is created.

Measurements on the stitched image covering both images A and B depend on the position of $(x_s, y_s)$, further referred to as stitch parameters.

The length d in pixels between pixels $(x_a, y_a)$ in image A and $(x_b, y_b)$ in image B is given by $$d = \sqrt{(x_a - (x_b + x_s))^2 + (y_a - (y_b + y_s))^2}.$$

Figure 4:
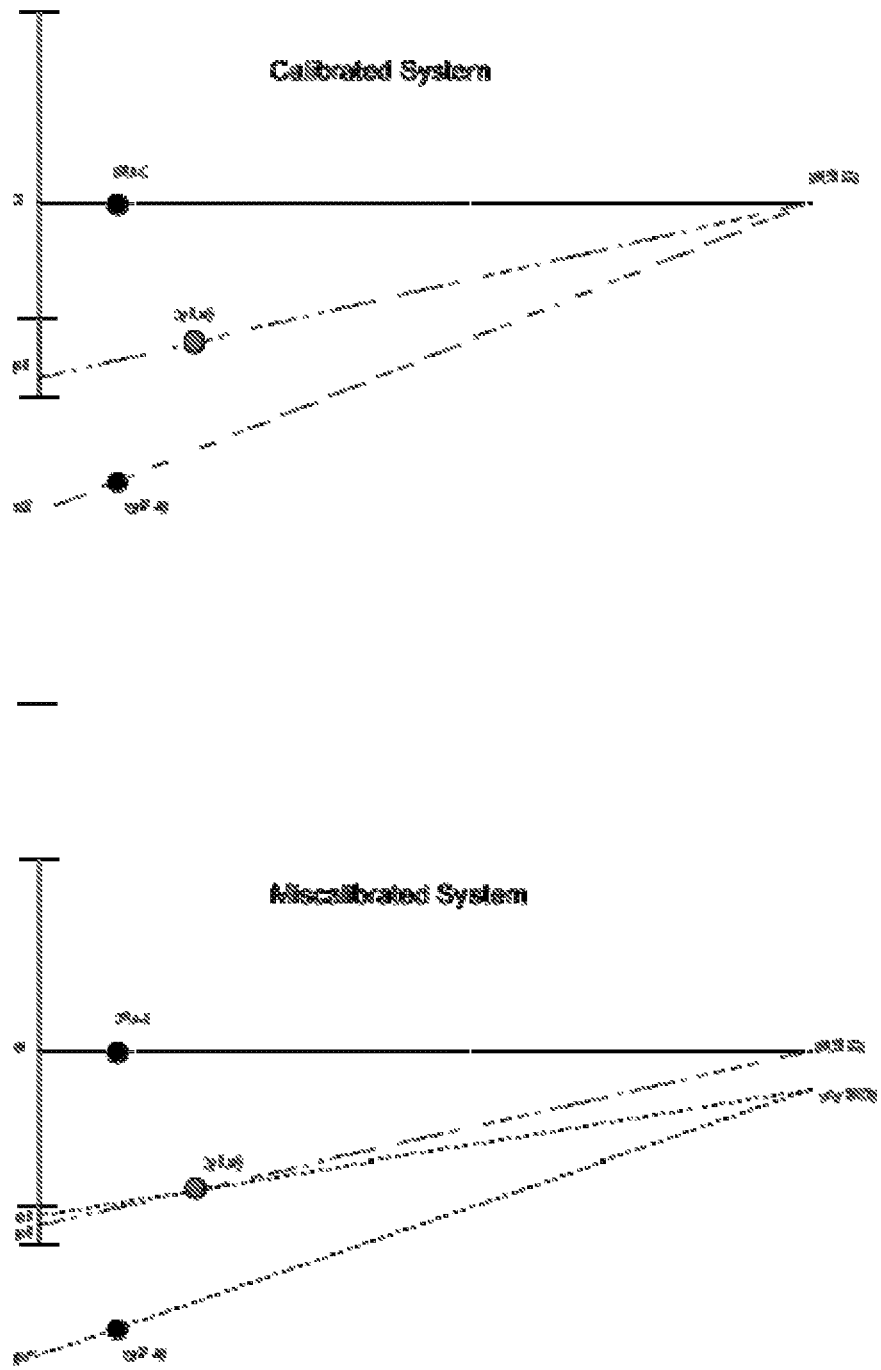
FIG. 4 is a schematic drawing which illustrates the effect of a wrongly calibrated system on a length measurement.

For a perfectly stitched image on a perfectly calibrated system without correction for the radiographic magnification factor and ignoring the x-component as illustrated in the top part of FIG. 4, the distance between the projections of points $(0, u)$ and $(y_2, u)$ is $$d_2 = p_2 = y_2 \frac{SID}{SID - u},$$

where u is the distance from the points to the detector and SID is the Source to Image Distance.

For a mis-calibrated system stitched on a reference point in the overlap zone, the distance $d'_2$ between the projections of the same points is given by $$d'_2 = p_1 + (p_2' - p_1').$$

Expressed in the following equations $$\frac{p_1}{SID} = \frac{y_1}{SID - u}$$

$$p_1' = d_y + q_1$$

$$p_2' = d_y + q_2$$

$$\frac{q_1}{SID} = \frac{y_1}{SID - v}$$

$$\frac{q_2}{SID} = \frac{y_2}{SID - u}$$

where $d_y$ is the amount of miscalibration and v is the distance between the detector and the point which is used as stitching reference, simplification for $d_2'$ gives $$d_2' = d_2 - d_y \left( \frac{SID}{SID - u} + \frac{SID}{SID - v} \right).$$

Suppose we have a system for which the calibration is incorrect in the vertical placement by 5 cm ($d_y = 5$), that the object we want to measure is 5 cm in front of the detector (u=5 cm) and it's projection is 40 cm ($d_2 = 40$), that the object which is used as reference for stitching is located 10 cm in front of the detector (v=10) and 20 cm lower than the top point of our object ($y_1 = 20$) and the X-ray source is located 180 cm from the detector (SID=180), the difference between $d_2$ and $d_2'$ is 1.51 mm. This illustrates that an error of 5 cm in the location of the X-ray source results in a measurement error of more than 1.5 mm for an SID of 180 cm.

Since measurements are important in long length imaging, it is essential to minimize the inaccuracies of the system and detect mis-calibrations. To achieve this, a radiation image is recorded of an object of known geometry superposed on the radiation image of the elongate body. The total image is generated by stitching partial images comprising part of the image of the elongate body and part of the image of the object of known geometry. If the theoretical computations of the positioning method return $(x_m, y_m)$ as the optimal stitch parameters and stitching the image based on the recorded image of the object of known geometry results in different stitch parameters $(x_g, y_g)$, the system is not positioned correctly. The cause of the difference between $(x_m, y_m)$ and $(x_g, y_g)$ can be an incorrect calibration of the system.

This incorrect calibration can be detected and reported in many different ways. For example, a warning to the user can be given under control of the computer performing the calculation if any of the following conditions is true $$|x_m - x_g| > \text{threshold}_{hor}$$

$$|y_m - y_g| > \text{threshold}_{vert}$$

$$\|x_m - x_g, y_m - y_g\| > \text{threshold}_{dist}$$

where the thresholds are predefined values. These thresholds can be determined experimentally on a well calibrated system or can be equal to the maximum expected difference based on the mechanical characteristics of the system. Other conditions or criteria could be statistical analysis of the observed values and the expected values, performance of confidence tests, statistical hypothesis tests or any other statistical tests to determine whether a value is acceptable within the limitations of the system.

Detection of Patient Movement

If the long length imaging sequence satisfies all acceptance criteria defined in the section above, detection of patient movement becomes important to determine the quality of the measurements in the stitched image. Because patient movement is inevitable for a method using multiple exposures, the radiographer normally has access to tools for the correction of the effects caused by the movement. These tools vary from manual techniques to complete automatic registration methods.

Suppose the radiographer positions the partial images with stitch parameters $(x_a, y_a)$ an indication of excessive patient movement can be given if one of the following conditions is true $$|x_a x_g| > \text{th}_{hor}$$

$$|y_a - y_g| > \text{th}_{vert}$$

$$\|x_a - x_g, y_a - y_g\| > \text{th}_{dist}$$

It is obvious that $(x_g, y_g)$ in the above equations can be replaced with $(x_m, y_m)$ or that other criteria can be used to determine if an indication of patient movement is given. The projected amount of patient movement is given by $$\text{movement}_{hor} = x_a - x_g$$

$$\text{movement}_{vert} = y_1 - y_g.$$

Implementation

Figure 5:
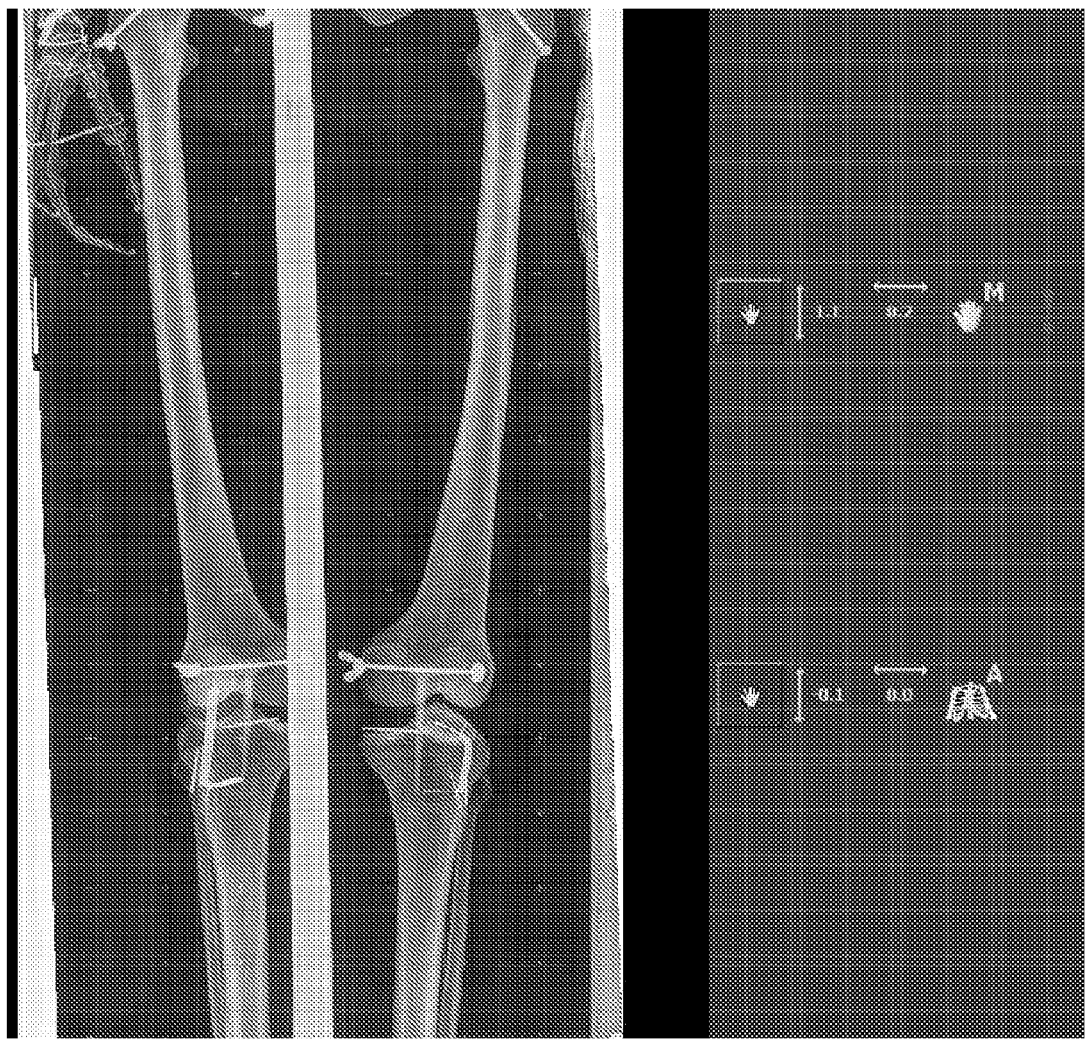
FIG. 5 is an illustration of a user interface implementation of the current invention.

A possible implementation of the invention is illustrated in FIG. 5 which shows a long length image consisting of three partial images. Two overlapping regions are shown: one just underneath the hands and the other at the height of the knees. To the right of the image, an indication of the amount of patient movement is given. For the bottom region, the amount of correction applied to obtain a correct stitched image is 1 mm vertical and 0 mm horizontal. This falls within the limits of the accuracy of our system and no warning indicator is shown.

For the top region, a vertical displacement of 1.1 cm and 2 mm is reported. This patient movement can easily be detected visually when looking at the right leg but is not apparently visible when looking the left leg in the image. To alert the user for possible errors caused by this patient movement, the exclamation mark is shown near the overlapping region.

The invention claimed is:

1. A method of generating radiation images of a body, each of said radiation images being generated by subjecting the same set of partial radiation images to a different computer-implemented stitching method, each of said partial radiation images comprising part of the radiation image of said body and being generated by multiple shot irradiation and read out of a direct radiography detector, wherein
one of said stitching methods is based on the reconstruction of the radiation image of an object of known geometry which is irradiated together said body so that each of said partial images comprises part of the radiation image of said body and part of the radiation image of said object of known geometry and wherein another of said stitching methods is performed on the basis of theoretical stitching parameters originating from the set-up used for said multiple shot irradiation and at least one value indicative of a deviation between the radiation images resulting from application of said different computer-implemented stitching methods to the same set of partial images is determined and a computer-controlled warning is generated if said value(s) exceeds a preset acceptance value(s).

2. A method according to claim 1 wherein one of said stitching methods is performed by user interaction and another is performed on the basis of reconstruction of the recorded image of said object of known geometry.

3. A method according to claim 1 wherein one of said stitching methods is performed by user interaction and another is performed on the basis of theoretical stitching parameters originating from the set-up used for said multiple shot irradiation.

4. A method according to claim 1 wherein said warning is an indication of patient movement.

5. A method of generating radiation images of a body, comprising:

generating a set of partial radiation images of said body by multiple shot irradiation and read out of a direct radiography detector;

stitching the partial radiation images into stitched radiation images using different stitching methods, wherein one of the stitching methods is based on the reconstruction of the radiation image of an object of known geometry which is irradiated together said body so that each of said partial images comprises part of the radiation image of said body and part of the radiation image of said object of known geometry and wherein another of said stitching methods is performed on the basis of theoretical stitching parameters originating from the set-up used for said multiple shot irradiation; and generating at least one value indicative of a deviation between the radiation images resulting from application of said different stitching methods to the same set of partial images; and generating a computer-controlled warning if said value exceeds a preset acceptance value.

\* \* \* \* \*